(12) United States Patent
Ory et al.

(10) Patent No.: US 6,408,656 B1
(45) Date of Patent: Jun. 25, 2002

(54) ISOELASTIC PROSTHETIC FILET STITCH FABRIC

(75) Inventors: François Régis Ory, Fontaines Saint Martin; Michel Therin, Lyons; Alfredo Meneghin, Villefranche sur Saone, all of (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 09/719,996

(22) PCT Filed: Jun. 23, 1999

(86) PCT No.: PCT/FR99/01512

§ 371 (c)(1),
(2), (4) Date: Feb. 28, 2001

(87) PCT Pub. No.: WO99/66860

PCT Pub. Date: Dec. 29, 1999

(51) Int. Cl.[7] .............................................. D04B 21/00

(52) U.S. Cl. ......................................... 66/195; 66/170

(58) Field of Search ........................... 66/195, 192, 203, 66/204, 205, 207, 233, 169 R, 170

(56) References Cited

U.S. PATENT DOCUMENTS

| 1,187,158 | A | * | 6/1916 | Mcginley | 66/195 |
|---|---|---|---|---|---|
| 3,118,294 | A | * | 1/1964 | Laethem | 66/195 |
| 3,124,136 | A |   | 3/1964 | Usher |  |
| 5,339,657 | A | * | 8/1994 | McMurray | 66/195 |
| 5,456,711 | A |   | 10/1995 | Hudson |  |
| 5,771,716 | A | * | 6/1998 | Schlussel | 66/195 |

FOREIGN PATENT DOCUMENTS

WO 97 08789 A 1/1997

* cited by examiner

*Primary Examiner*—Danny Worrell
(74) *Attorney, Agent, or Firm*—Oliff & Berridge, PLC

(57) ABSTRACT

This knit is produced on the basis of a biocompatible polymer material monofilament, whose pattern is defined by a front lap and a rear lap of yarns knitted together and determines a plurality of cells each having a substantially polygonal shape. The pattern gives the knit a multidirectional tensile behavior such as obtained by a front lap capable of being obtained by knitting according to a scheme 5-4/4-3/2-1/0-1/1-2/3-4 and by a rear lap capable of being obtained by knitting according to a scheme 0-1/1-2/3-4/5-4/4-3/2-1.

14 Claims, 4 Drawing Sheets

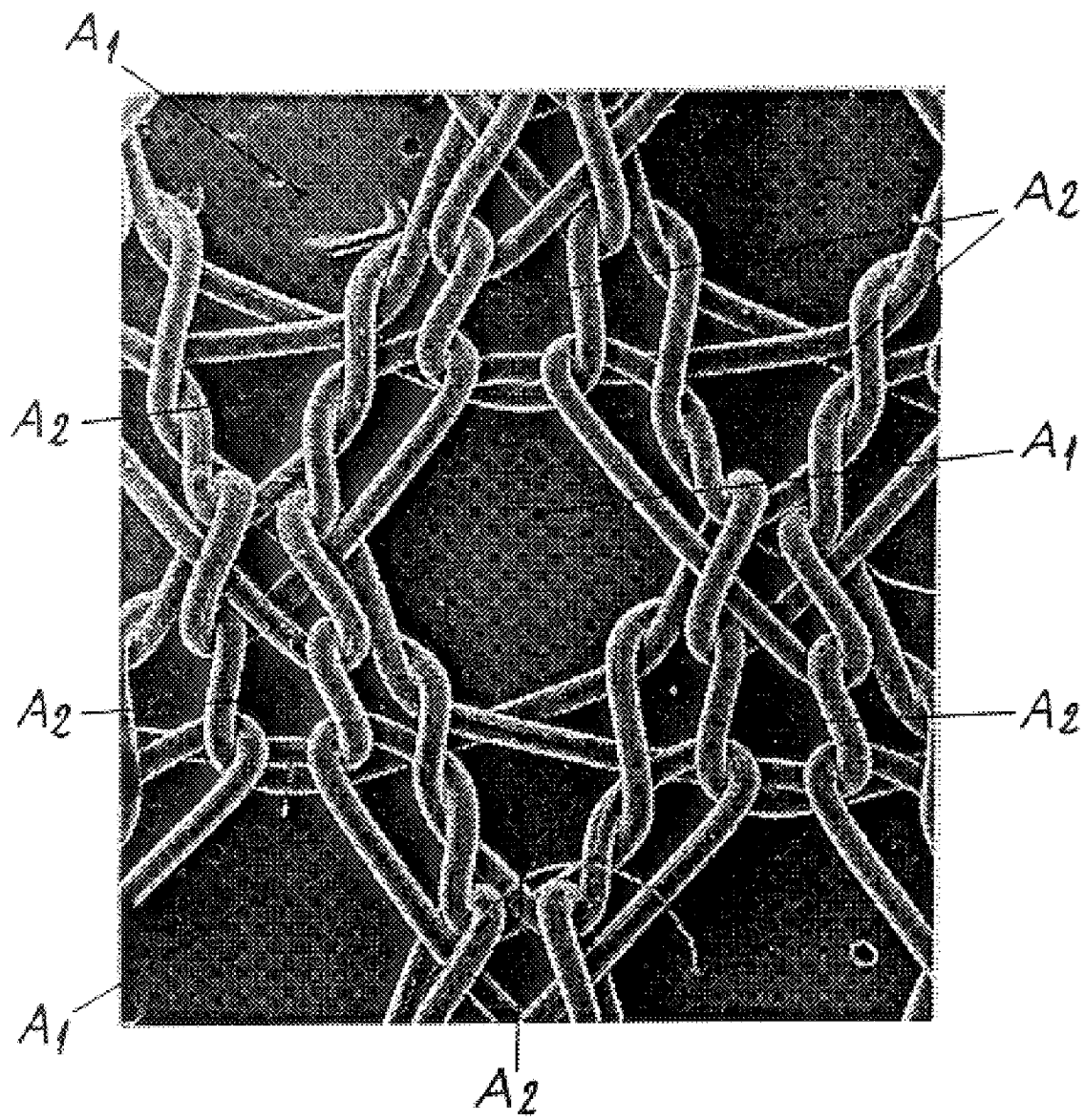

AR  AV 5 4 3 2 1
AR.AV

PRIOR ART

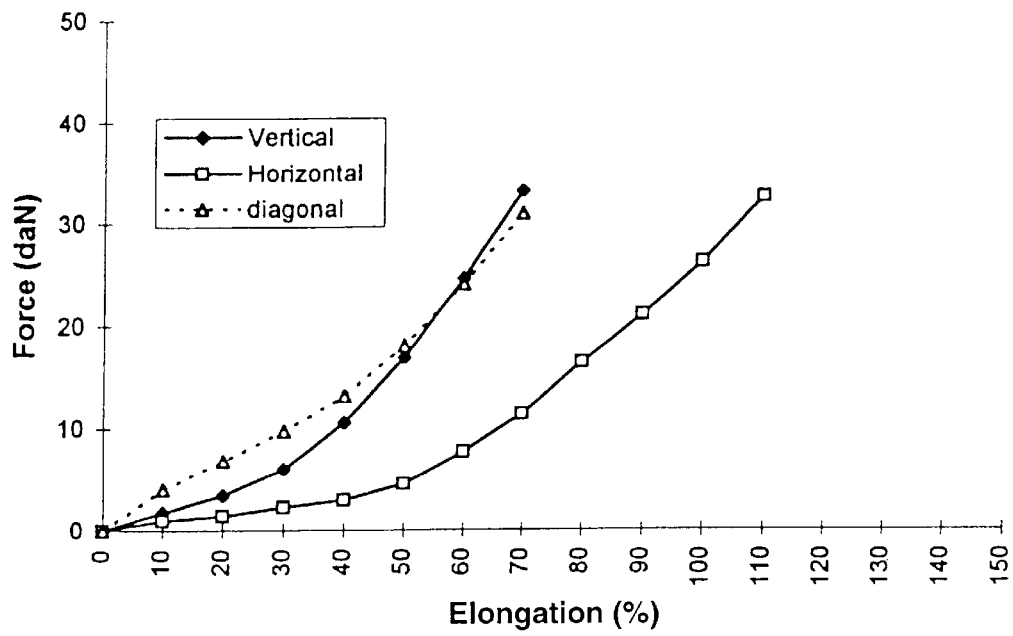
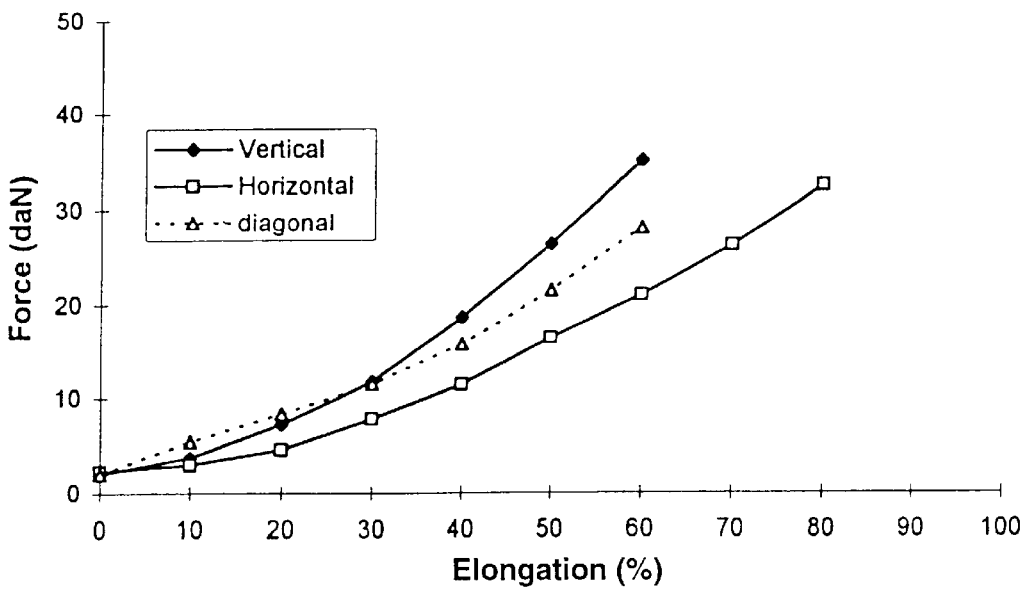

ISOELASTIC PROSTHETIC FILET STITCH FABRIC

BACKGROUND OF THE INVENTION

1. Field of the Invention

The present invention relates to an isoelastic open knit useful in particular in parietal and/or visceral surgery, but which can also be used in other areas of surgery.

2. Description of Related Art

The present invention will be described more particularly by referring to a prosthetic knit of said type, intended to be used for the repair of hernias or eventrations. The abdominal wall consists of muscles which are physiologically deformable in all directions, and therefore an ideal reinforcement must follow these physiological deformations whilst providing additional strength to a weakened wall. Even though there is a lack of published data, the lower limit of tensile strength of a prosthetic knit for the repair of hernias or eventrations is in the region of 10 kg, when tested according to the NFG 07-001 standard.

In the present application, the expressions given below have the following meanings:

the term "fabric" means an assembly of yarns, obtained in particular by knitting and/or weaving;

the term "biocompatible polymer material" means a material, or its possible products of degradation in a biological medium, which induces no effect which is toxic or contrary to the sought effect, once implanted in the body.

For a long time, surgeons have used flat prosthetic fabrics, that is to say two-dimensional ones, to repair or replace any part of the body, such as an aponeurosis or a muscular wall, destroyed or damaged, for example as a result of a traumatism. Consequently there are now a large number of such prosthetic fabrics manufactured or obtained according to various processes, for example weaving, knitting or molding, and which have often been designed to carry out specific functions within the body in which they are implanted. Such prosthetic fabrics are described for example in documents U.S. Pat. No. 5,569,273, WO-A-96/03091 and EP-A-0797962, which divulge the knitting of monofilaments or multifilaments of polypropylene or of polyester.

Patent application PCT WO-A-97/02789 describes an open knit based on a monofilament of a biocompatible polymer material, the pattern of said knit defining a plurality of cells having a substantially polygonal shape. The fabric is intended in particular for the repair of hernias, and is based on a polypropylene monofilament, of diameter 0.15 mm, whose knitting pattern is defined by two laps of yarns knitted together according to the following scheme:

front lap: 2/0-2/4-2/0-4/6-4/2-4/6;
rear lap: 4/6-4/2-4/6-2/0-2/4-2/0.

SUMMARY OF THE INVENTION

The purpose of the invention described in this document is to provide a fabric with a better transparency in order to facilitate its use in laparoscopic repair techniques. Furthermore, it is mentioned, in page 1, lines 31–32 of the published application, that the knit must have the physical characteristics and performance of conventional repair prosthetic fabrics.

However, such conventional fabrics have several disadvantages, related to the very structure of the fabric, or to the choice of the basic material used for forming the yarns, or else to the way in which the prosthetic fabric is manufactured. Thus, the mechanical properties of the conventional fabrics obtained are extremely variable from one fabric to another depending on the orientation of the specimen: vertical (also called production direction or columns) or horizontal (also called cross direction or rows). By way of example, the knitting scheme used in document WO-A-97/02789 makes it possible to obtain a knit which is about two times stronger in weft than in warp, and this corresponds entirely with the properties of conventional fabrics. A recent publication compares the mechanical properties of the principal fabrics used up to the present time (cf. Table 1 below). The differences range from 1 to 40 for the tear strength and from 1 to 8 for the tensile strength. The values of elongation under physiological loads or at break are rarely mentioned (even less so in the diagonal direction), even though they are an important parameter for the functionality of this type of product.

TABLE 1

|  |  | Marlex ® | Prolene ® | Mersilene ® |
|---|---|---|---|---|
| Manufacturer |  | Bard | Ethicon | Ethicon |
| Type |  | PP mono-filament | PP bi-filament | PET multi-filament |
| Weight/m$^2$ |  | 95 | 108.5 | 39.5 |
| Tensile strength (daN) | vertical | 43 | 60 | 20 |
|  | horizontal | 57 | 77 | 10 |
| Tear strength (daN) | vertical | 0.7 | <0.1 | 0.6 |
|  | horizontal | 4 | 4.4 | 0.7 |

Source: U. Klinge et al: Veränderung der Bauchwandmechanik nach Mesh-Implantation. Langenbecks Arch Chir (1996) 381:323–332.

Furthermore, it is also known that the tissual reaction to an implant is the result of a normal cicatrization process. Any tissual surgical traumatism is followed by a cascade of physiological events, the principal timings of which are as follows:

t0: surgical traumatism, capillary breakage;
t0 plus a few minutes: coagulation, fibrinous network, release of chemotactic factors;
t0 plus 12 to 48 hours: polynuclear dominant luecocytic afflux;
t0 plus 4 to 8 days: fibroblastic afflux;
t0 plus 24 hours to 5 days: macrophagic dominant leucocytic afflux;
t0 plus 8 to 21 days: conjunctive differentiation of the cicatricial reaction;
t0 plus 15 to 180 days: cicatricial remodeling on contact with the implant.

Even though in certain cases the exact mechanisms are as yet unknown, particularly with regard to the determinism of the intensity of the reaction, it therefore appears that the first 8 days are determinant since they condition the fibroblastic afflux.

In non-bony tissues, the equilibrium of the reaction leads to the formation of a fibroconjunctive membrane which constitutes the interface between the implanted material and the surrounding healthy tissue. Whatever the type of implant may be, the zone under the direct influence of a biocompatible conventional material is a minimum of about 50 micrometers.

Furthermore, in the treatment of parietal inadequacies (principally hernias and eventrations), the prosthetic fabric has the task of providing additional mechanical strength to the surgical reconstruction, and its effectiveness and its local tolerance are directly related to the degree to which its tissual integration is intimate and early.

The Applicant has established by its own studies that several aspects influence tissual response to a prosthetic implant:

the constituent material of the prosthesis and its possible products of degradation in a biological medium must not induce any effect which is toxic or contrary to the sought effect. In the case of a prosthetic fabric implanted for long-term use, the aging of the material and its consequences (wear, expulsion of components, etc.) is the most difficult factor to anticipate; only raw materials validated over a long period provide maximum safety;

in a manner of speaking, as the organism sees only the surface of the material, the properties of the latter are of significant importance. Among all the surface parameters, the surface energy and the roughness play an important role. In fact, when it is sought to promote cellular integration, the surface must be absorbent (high surface energy) and smooth on a cellular scale (of the order of one micron);

only the porosity accessible by the organism is useful with regard to the anchoring of the prosthetic fabric. This porosity must be interconnected in a given volume, and there must be sufficient space for a significant cellular penetration (of the order of about 20 to 80 micrometers), and for a tissual differentiation (100 to 300 micrometers generally constitute a minimum for complete differentiation). It has been recalled previously that the minimum thickness of the tissual reaction is of the order of 50 micrometers, which means that, for porosity sizes less than 100 micrometers, the rehabilitation tissue will be entirely under the influence of the presence of the implant with little possibility of complete tissual differentiation occurring;

vascularization and the biomechanical environment of the receiving site condition the intensity of the tissual response. A richly vascularized site (skin, muscles, etc.) will react faster and more intensely than less vascularized tissues (forward chamber of the eye, bone, etc.). Furthermore, the very nature of the receiving site conditions the capacity of identical regeneration of the wounded tissue. Bone, connective tissues, mucous membranes, certain parenchymes (the liver for example) can regenerate identically without significant fibrous cicatrice. On the other hand, other very specialized tissues (muscles, nerve tissues, etc.) have lost all capacity of regeneration, the cicatrization of these tissues therefore takes place only by fibrosis;

surgical traumatism constitutes one of the principal triggering factors of the previously described cascade reaction. The greater it is, the more intense will be the reaction and the more pronounced will be its consequences (cicatrization time, fibrous after-effects, pain, etc.);

reinforcement becomes more effective and its local tolerance becomes better if its tissual integration is intimate and early. In order to be intimate and early without the formation of peripheral fibrous shell, the macroporosities of the implant must, as widely as possible, be open to the exterior and the elasticity of the reinforcement must allow it to follow the physiological deformations of the wall. The upper limits being given by the mechanical strength (>10 Kg in the standard NFG07-001 test) of the fabric, the ability to be manipulated by the surgeon and the impossibility of hernia recurrence through the pores of the fabric of maximum diameter 5 mm).

Considering the above, one of the objectives of a good prosthetic fabric is a tissual integration which is as fast as possible, providing a mechanically satisfactory anchoring without extensive fibrosis, which is a source of discomfort and pain.

The present invention describes a new type of knitted reinforcement providing isotropic elastic mechanical properties, that is to say substantially equivalent in all directions whilst retaining high porosity for a better tissual rehabilitation and sufficient rigidity for satisfactory surgical manipulation.

The fabric in question is an isoelastic prosthetic open knit based on a monofilament of a biocompatible polymer material, whose pattern is defined by a front lap and a rear lap of yarns knitted together and whose pattern determines a plurality of cells each having a substantially polygonal shape.

According to the invention, the pattern gives the knit a multidirectional tensile behavior such as obtained by a front lap capable of being obtained by knitting according to a scheme 5-4/4-3/2-1/0-1/1-2/3-4 and by a rear lap capable of being obtained by knitting according to a scheme 0-1/1-2/3-4/5-4/4-3/2-1.

The applicant has discovered that a prosthetic knit based on a biocompatible monofilament, such as defined above, has the following advantages:

the knit is flexible and not very dense in material, the weight per m$^2$ being reduced, for example by at least 30%, in comparison with equivalent products on the market, which makes it possible to obtain better local tolerance;

the knit has sufficient firmness (spring effect during imposed deformations) for easy manipulation by the surgeon;

the knit cannot become unraveled whatever cuts may be made by the surgeon, with few filament drops along the cutting line, unlike the known fabrics;

the isoelasticity, illustrated by relatively linear slopes of stress/strain curves according to the direction of tension of the knit, makes it possible to obtain biomechanical adequation with the abdominal wall;

the knit is relatively transparent for better visibility of the covered anatomical structures in particular during laparoscopic positioning;

the knit is porous with principal openings of the order of one millimeter for better cellular penetration and in-depth conjunctive differentiation without peripheral fibrous shell phenomena, a potential source of discomfort and pain.

In a preferred embodiment of the invention, the knit has a tensile behavior defined by a ratio of measurable values, for example the tensile strength, in the vertical/horizontal/diagonal stress directions, of between 0.9:1:1.5 and 1.5:1:1.5.

Preferably, the knit has at least any one of the following properties:

the stress at break of the knit according to the NFG07-001 standard is of the order of 25 daN in all directions;

the elongation at break of the knit according to the NFG07-001 standard is of the order of 70% in all directions;

the initiated-tear strength of the knit according to the NFG07-001 standard is of the order of 5 daN;

the elongation under stress of 10 daN of the knit according to the NFG07-001 standard is of the order of 35% in all directions.

Preferably, the open knit is based on a monofilament of biocompatible polymer material chosen from the group consisting of polypropylene, polyester and polyamide, and preferably is a polypropylene monofilament.

Preferably, the diameter of the monofilament is between 0.12 mm and 0.18 mm, and preferably is 0.15 mm.

Preferably, the pattern of the knit forms unblocked open meshes defining principal cells surrounded by cells of smaller size, favoring rehabilitation.

Advantageously, each principal cell has a diameter of from about 1 mm to about 2 mm, and preferably a diameter of between 1.5 mm and 1.9 mm, whilst the smaller cells have a diameter of between 0.4 and 0.8 mm and preferably of between 0.6 and 0.7 mm.

The thickness of the knit is between 0.5 mm and 1 mm, and preferably is at most equal to 0.7 mm.

Preferably, the knit has a weight per unit area of between 50 g/m$^2$ and 100 g/m$^2$, and preferably a specific weight of about 75 g/m$^2$.

Another subject of the invention is a parietal and/or visceral prosthesis, obtained with a knit such as defined above.

Yet another subject of the invention is the use of a knit according to the invention such as defined, in order to obtain a prosthetic product for surgical use, in particular for manufacturing a parietal and/or visceral prosthesis.

BRIEF DESCRIPTION OF THE DRAWINGS

The present invention will be better understood with regard to the detailed description of a preferred embodiment of the invention, given by way of example, referring to the accompanying figures, wherein:

FIG. 1 is a front view of an isoelastic prosthetic open knit according to the invention, taken by electron scanning microscopy with a magnification of 20 times;

FIG. 4 is a graph of stress/strain curves according to the direction of tension of the isoelastic knit of FIG. 1;

FIG. 5 is a graph of stress/strain curves of an isoelastic open knit according to FIG. 1, under a prestress of 2 daN.

DETAILED DESCRIPTION OF PREFERRED EMBODIMENT

Referring to FIG. 1, the knit according to the present invention is an open knit, made of polypropylene monofilament of diameter 0.15 mm, produced on a warp knitting machine or on a rachel knitting machine with two laps or guide bars threaded, one full, one empty, moving symmetrically. The pattern is an open mesh atlas with progressions under two and three needles. This makes it possible to obtain similar values of horizontal elasticity and vertical and diagonal elasticity. In this way a knit is obtained with relatively balanced multidirectional tensile characteristics.

FIG. 1 shows well that each principal cell A1 is surrounded by peripheral cells A2 of smaller size aerating the knit, increasing its porosity by eliminating any local massing of yarns, and improving its transparency and the possibilities of rehabilitation.

The knitting scheme is shown diagrammatically in FIGS. 2a and 2b, and is as follows, namely:

for the rear lap: 0-1/1-2/3-4/5-4/4-3/2-1;

for the front lap: 5-4/4-3/2-1/0-1/1-2/3-4.

Figure 2A:
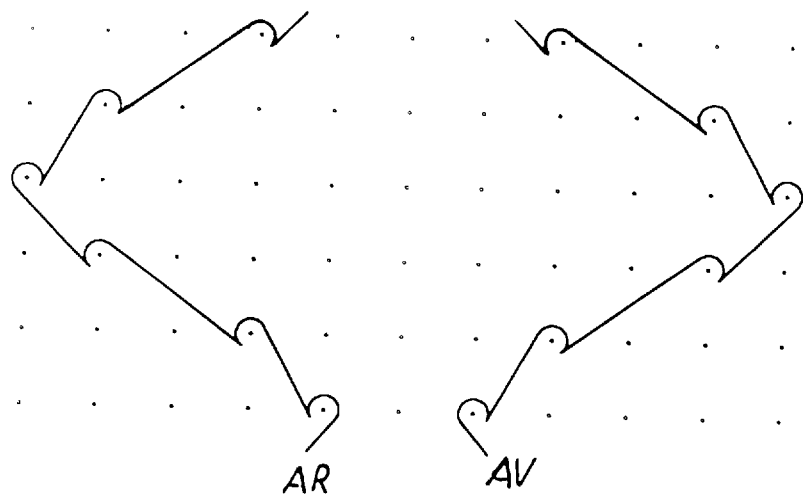
FIG. 2a is a simplified diagrammatic drawing of a front yarn (AV) and of a rear yarn (AR) of the knitting pattern of the isoelastic prosthetic knit according to FIG. 1.

FIG. 2a shows only one front yarn (AV) and one rear yarn (AR) of the pattern in order to show the movements of the yarns more clearly. Thus it is observed that the yarns of the fabric according to the invention move under a total of five needles, which makes it possible to obtain a better holding of the yarns with less risk of unraveling of the edges, and of undoing.

Figure 2B:
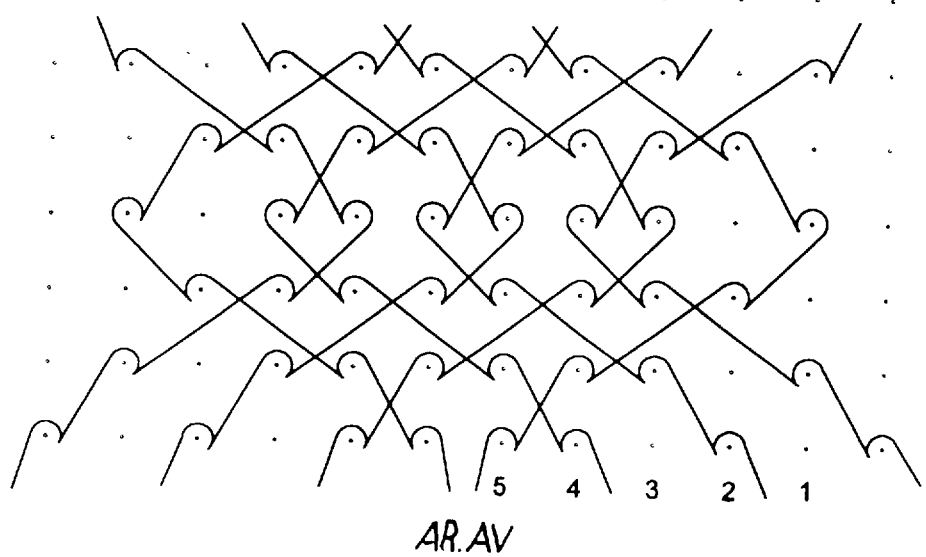
FIG. 2b is a simplified diagrammatic drawing of the knitting pattern of the isoelastic prosthetic knit according to FIG. 1.
Figure 3A:
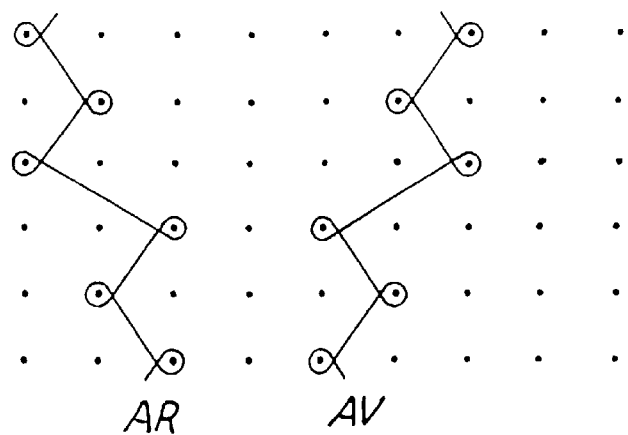
FIG. 3a is a simplified diagrammatic drawing of a front yarn (AV) and of a rear yarn (AR) of the knitting pattern of a prosthetic knit according to the prior art.
Figure 3B:
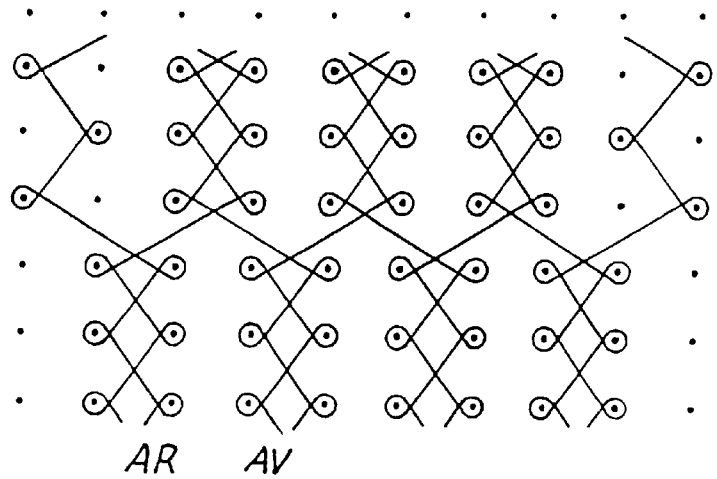
FIG. 3b is a simplified diagrammatic drawing of the knitting pattern of a prosthetic knit according to the prior art.

FIGS. 3a and 3b show the diagram of the pattern used to obtain a prosthetic knit according to application WO-A-97/02789, and make it possible to see the differences with respect to the isoelastic knit according to the invention by comparison with FIGS. 2a and 2b. Thus it is observed that the yarns of the knit of the prior art move under three needles and not five as in the knit of the present invention, which leads, in particular, to greater dropping of filaments during the cutting of the knit by the surgeon, in comparison with the knit of the invention.

Furthermore, the use of open meshes in the knit according to the invention in comparison with the closed meshes of the fabric of application WO-A-97/02798 (cf. FIGS. 3a and 3b) allows greater freedom in the knitting and therefore better control of its elasticity.

Examples of results for a knit produced from 0.15 mm diameter polypropylene monofilament, heat set under horizontal tension at 150° C. (weight per m$^2$: approximately 75 g), are given in Table 2 below.

TABLE 2

|  | Vertical | Horizontal | Diagonal |
| --- | --- | --- | --- |
| Elongation at break (%) NFG07-001 standard | 70 | 107 | 68 |
| Elongation under 10 daN (%) NFG07-001 standard | 40 | 67 | 31 |
| Initiated-tear strength (daN) NFG07-149 standard | 5.6 | 5.1 | — |
| Burst characteristics NFG07-112 standard |  |  |  |
| Pressure in MPa |  | 0.82 |  |
| compression in mm |  | 14.4 |  |

It is observed that whatever the orientation of the tested sample may be, the tensile strength and the initiated-tear strength are relatively homogeneous. With the type of yarn used for this test, the tensile strength is distinctly better than the minimum values required for this kind of reinforcement (10 to 15 daN). The initiated-tear strength constitutes an important parameter which illustrates the firmness of the anchorings at the points of attachment or during stresses on the reinforcements at cut-out and complex contours. This tear strength is very much higher than those measured for the equivalent products currently on the market (cf. Table 1).

FIG. 4 shows that, at an equivalent stress, the vertical and diagonal directions have curves which are practically superimposed. If it is considered that in open surgery, and more particularly in the case of treatment of eventrations, the reinforcements are implanted with a moderate initial tension which can be estimated to be of the order of 2 daN, then the stress/strain curves as a function of the direction of tension become very close to each other (cf. FIG. 5). The moderately greater elasticity in the horizontal direction can provide latitude to the surgeon with regard to the privileged direction of the allowed deformations. In fact, many surgeons consider that the elasticity requirements are greater in the superior-inferior direction, because there is a frequent flexion of the vertebral column by contraction of the big straight muscles of the abdomen, than in the lateral-lateral direction, which corresponds more to a progressive distension of the abdominal band. The fabric according to the present invention makes it possible to accommodate this surgical preference in a satisfactory manner, without however losing the advantageous mechanical properties in the other directions of tension.

What is claimed is:

1. An isoelastic prosthetic open knit based on a monofilament of a biocompatible polymer material, whose pattern is defined by a front lap and a rear lap of yarns knitted together and determines a plurality of cells each having a substantially polygonal shape, characterized in that said pattern gives the knit a multidirectional tensile behavior obtained by a front lap capable of being obtained by knitting according to a scheme 5-4/4-3/2-1/0-1/1-2/3-4 and by a rear lap capable of being obtained by knitting according to a scheme 0-1/1 -2/3-4/5-4/4-3/2-1.

2. The knit as claimed in claim 1, characterized in that its weave forms unblocked open meshes defining principal cells (A1) and peripheral cells (A2) surrounding the latter but of smaller size.

3. The knit as claimed in claim 2, characterized in that each cell (A1) has a diameter of from about 1 mm to about 2mm whilst the peripheral cells (A2) have a diameter of between 0.4 and 0.8 mm.

4. The knit as claimed in claim 1, characterized in that its thickness is between 0.5 mm and 1 mmn.

5. The knit as claimed in claim 4, characterized in that its thickness is at most equal to 0.7 mm.

6. The knit as claimed in claims 1, characterized in that its stress at break according to the NFG07-001 standard is of the order of 30 daN in all directions.

7. The knit as claimed in claims 1, characterized in that its elongation at break, measured with a moderate initial tension, of the order of 2 daN, is of the order of 80% in all directions.

8. The knit as claimed in claim 1, characterized in that its initiated-tear strength according to the NFG07-003 standard is of the order of 5 daN.

9. The knit as claimed in claim 1, characterized in that its elongation under stress of 10 daN measured with a moderate initial tension, of the order of 2 daN, is of the the order of 35% in all directions.

10. The knit as claimed in claim 1, characterized in that it has a weight per unit area of between 50 g/m$^2$ and 100 g/m$^2$.

11. The knit as claimed in claim 10, characterized in that it has a specific weight of about 75 g/m$^2$.

12. The knit as claimed in claim 1, characterized in that it is produced on a warp knitting machine or on a rachel hitting machine with two laps or guide bars threaded, one fill, one empty, moving symmetrically, the pattern being an open mesh atlas with progressions under two and three needles.

13. A parietal and/or visceral prosthesis, obtained with a knit as claimed in claim 1.

14. The knit as claimed in claim 2, characterized in that each cell (A1) has a diameter of from about 1.5 mm to about 1.9 mm, whilst the peripheral cells (A2) have a diameter of between 0.4 mm and 0.8 mm.

* * * * *